United States Patent
Baumgartl et al.

(10) Patent No.: US 10,819,624 B2
(45) Date of Patent: Oct. 27, 2020

(54) METHOD AND FACILITY FOR COMMUNICATION IN A MEDICAL IMAGING FACILITY AND MEDICAL IMAGING FACILITY

(71) Applicant: Siemens Healthcare GmbH, Erlangen (DE)

(72) Inventors: Rudi Baumgartl, Erlangen (DE); Nikolaus Demharter, Dormitz (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 50 days.

(21) Appl. No.: 16/167,683

(22) Filed: Oct. 23, 2018

(65) Prior Publication Data

US 2019/0123998 A1    Apr. 25, 2019

(30) Foreign Application Priority Data

Oct. 25, 2017  (EP) ..................................... 17198298

(51) Int. Cl.
  *H04L 12/725*    (2013.01)
  *H04L 1/00*    (2006.01)
  (Continued)

(52) U.S. Cl.
  CPC ........ *H04L 45/306* (2013.01); *G01R 33/3692* (2013.01); *G16H 30/20* (2018.01);
  (Continued)

(58) Field of Classification Search
  None
  See application file for complete search history.

(56) References Cited

U.S. PATENT DOCUMENTS 3,599,160 A    8/1971  Nestle et al.
6,288,800 B1 *  9/2001  Izumi ................. H04N 1/00103
                                                358/442
(Continued)

FOREIGN PATENT DOCUMENTS

CN    104635189 A    5/2015
CN    105807244 A    7/2016
(Continued)

OTHER PUBLICATIONS

LTU-T: "ITU-T Interfaces for the optical transport network G.709/Y.1331 ", XP055647169, [gefunden am Nov. 27, 2019]; 2016.
(Continued)

*Primary Examiner* — Chi H Pham
*Assistant Examiner* — Raul Rivas
(74) *Attorney, Agent, or Firm* — Harness, Dickey & Pierce, P.L.C.

(57) ABSTRACT

A method for communication between at least two computing facilities of a medical imaging facility via a single communication line is disclosed. In the method, communication information assigned to different communication types received in each case via a dedicated data input is merged to form data structures of a defined size to be transmitted via the communication line. The data structures are transmitted cyclically via the communication line with an interval of one cycle time and communication information of the different communication types is extracted from data structures received via the communication line and output at data outputs assigned to the respective communication types. The communication types include a first packet-oriented communication type and a second isochronous communication type corresponding to isochronous direct channel communication.

15 Claims, 2 Drawing Sheets

(51) Int. Cl.
  *H04L 29/06*   (2006.01)
  *G16H 30/20*   (2018.01)
  *G01R 33/36*   (2006.01)
  *H04L 29/08*   (2006.01)

(52) U.S. Cl.
  CPC ............ *H04L 1/0041* (2013.01); *H04L 69/10* (2013.01); *H04L 67/12* (2013.01)

(56) References Cited

U.S. PATENT DOCUMENTS

| | | | |
|---|---|---|---|
| 8,457,990 B1* | 6/2013 | Reicher | G06Q 10/10 |
| | | | 705/3 |
| 2008/0136417 A1 | 6/2008 | Baumgartl et al. | |
| 2009/0096546 A1 | 4/2009 | Demharter et al. | |
| 2009/0137898 A1 | 5/2009 | Demharter et al. | |
| 2009/0251141 A1 | 10/2009 | Baumgartl et al. | |
| 2010/0257190 A1* | 10/2010 | Farkash | G06F 19/321 |
| | | | 707/760 |
| 2014/0046617 A1 | 2/2014 | Campagna | |
| 2015/0312781 A1* | 10/2015 | Chowdhary | H04W 24/04 |
| | | | 455/424 |
| 2016/0174928 A1 | 6/2016 | Demharter | |
| 2016/0187443 A1 | 6/2016 | Liu et al. | |
| 2016/0285547 A1* | 9/2016 | Loprieno | H04J 3/14 |

FOREIGN PATENT DOCUMENTS

| | | |
|---|---|---|
| CN | 106301659 A | 1/2017 |
| DE | 102006052437 A1 | 5/2008 |
| DE | 102007058872 A1 | 4/2009 |
| DE | 102008017819 B3 | 12/2009 |
| DE | 102012213948 A1 | 2/2014 |

OTHER PUBLICATIONS

P Nagasiva Kumar et al: "Analysis of Optical Time Division Multiplexing Using Packet Interleaving Scheme", International Journal of Scientific and Research Publications, XP055647205, Gefunden im Internet: URL:http://www.ijsrp.org/research-paper-0413/ljsrp-p1674.pdf; (gefunden am Nov. 27, 2019); 2013.

Jiqiang Xia et al: "Real-time and reliability analysis of timetriggered CAN-bus", Chinese Journal of Aeronautics, vol. 26, No. 1, pp. 171-178, XP055647309, Amsterdam, NL; ISSN: 1000-9361, DOI: 10.1016/j.cja.2012.12.017; 2013.

Jianxin Liu et al: "The analysis and test of real-the performance for time-triggered CAN bus", Automation and Logistics, 2008. ICAL 2008. IEEE International Conference on, IEEE, Piscataway, NJ, USA, pp. 3005-3009, XP031330185, ISBN: 978-1-4244-2502-0; 2008.

Ghariya Rutika et al: "Real time data transfer using fiber optic communication", 2016 10th International Conference on Intelligent Systems and Control (ISCO), IEEE, pp. 1-3, XP032989088, DOI: 10.1109/ISCO.2018. 7726905; [gefunden am Oct. 31, 2016 ]; 2016.

Anonymous: "Statistical time-division multiplexing—Wikipedia", XP055389944, Gefunden im Internet:URL:https://en.wikipedia.org/wiki/Statistical_timedivision_multiplexing; [gerfunden am Jul. 11, 2017]; 2017.

European Office Action dated May 6, 2019.

Chinese Office Action and English translation thereof dated Apr. 15, 2020.

* cited by examiner

METHOD AND FACILITY FOR COMMUNICATION IN A MEDICAL IMAGING FACILITY AND MEDICAL IMAGING FACILITY

PRIORITY STATEMENT

The present application hereby claims priority under 35 U.S.C. § 119 to European patent application number EP 17198298.6 filed Oct. 25, 2017, the entire contents of which are hereby incorporated herein by reference.

FIELD

Embodiments of the invention generally relate to a method and a communication facility for communication between at least two computing facilities of a medical imaging facility, in particular a magnetic resonance facility, via a single communication line. In addition, the invention relates to a medical imaging facility, in particular a magnetic resonance facility.

BACKGROUND

Present-day medical imaging facilities include a plurality of components, which can be used for control, implementation of peripheral functions, the actual imaging and further tasks. Many of these components comprise computing facilities, which communicate with other computing facilities of other components and/or the same component for the operation of the medical imaging facility, for example for outputting and receiving control commands and/or image and/or scan data. For example, a central control computer is frequently used in present-day magnetic resonance facilities or magnetic resonance systems wherein said central control computer communicates with computing facilities of further components, for example with a peripheral unit, a transmit unit, a receive unit and a gradient unit. The peripheral unit can in turn communicate with peripheral subunits; in addition, said units communicate with one another and/or with expansion units, for example additional receive units and the like. The individual components are therefore connected by a plurality of cables and lines to one another and also to the central control computer/image-calculating computer. Herein, the different components or the computing facilities have different requirements for information transmission.

For example, the communication information to be transmitted is control information with and without a time reference, wherein another common application in medical imaging relates to isochronous data streams as communication information with which a direct time reference is to be re-established from the clock pulse frequency/clock pulse rate. The first type of communication information cited is typically transmitted in a packet-oriented manner, the second type of communication information is typically transmitted in a channel-oriented manner, i.e. via an isochronous direct channel connection.

Consequently, a plurality of communication interfaces with different communication protocols exist side by side. For example, PCI Express, ISO, RS 232, SPI, USB, CAN/CANopen and various specialized proprietary protocols are used as communication protocols in modern magnetic resonance facilities.

This plurality of communication interfaces with different communication protocols results in a high level of technical effort, a high space requirement, complex cabling and hence overall very high costs for the medical imaging facility, in particular magnetic resonance facility.

DE 102006052437 A1 and DE 102008017819 B3 in each case show the structure of an MR control system, DE 102007058872 A1, US 20090137898 A1, US 20160174928 A1 in each case show devices for data transmission in an MR system.

SUMMARY

An embodiment of the invention is based on improving communication within a medical imaging facility with respect to the different requirements for different types of communication information.

Embodiments of the invention are directed to a method for communication between at least two computing facilities of a medical imaging facility, a communication facility and a medical imaging facility. Advantageous embodiments are found in the claims.

In a method according to an embodiment of the invention for communication between at least two computing facilities of a medical imaging facility, in particular a magnetic resonance facility, via a single communication line it is provided that communication information assigned to different communication types received in each case via a dedicated data input is merged to form data structures of a defined size to be transmitted via the communication line, wherein the data structures are transmitted cyclically with an interval of one cycle time via the communication line and communication information of the different communication types is extracted from data structures received via the communication line and output at data outputs assigned to the respective communication types, wherein the communication types comprise a first packet-oriented communication type and a second isochronous communication type corresponding to isochronous direct channel communication.

A communication facility, according to an embodiment of the invention, for communication between at least two computing facilities of a medical imaging facility, in particular a magnetic resonance facility comprises:

a communication line and for each computing facility in each case a communication-interface assembly connected to the communication line, wherein the communication interface assemblies in each case a separating-and-merging unit for merging communication information assigned to different communication types received in each case via a dedicated data input into data structures of a defined size to be transmitted via the communication line and for cyclic transmission of the data structures with an interval of one cycle time via the communication line and for the extraction of communication information of the different communication types from data structures of the respective other communication-interface assembly received via the communication line and forwarding to data outputs assigned to the respective communication types, wherein a packet communication unit for the provision and reception of communication information of the first communication type is connected to a data-input-data-output pair assigned to a first packet-oriented communication type and an isochronous communication unit providing and receiving isochronous data as communication information is connected to a data-input-data-output pair assigned to the second communication type corresponding to isochronous direct channel communication. Therefore, the communication facility is embodied to carry out the method according to the invention.

According to an embodiment of the invention, a novel type of communication interface that implements a communication protocol that can be called a UCI (unified communication interface). A UCI is serial point-to-point communication protocol implementing at least two different communication types by way of time-division multiplexing, preferably with the additional use of protection mechanisms. This means that each communication type is assigned a fixed portion (at least one slot) of the data structure (frame) with a fixed invariable size/length. The communication information of the different communication types, which is provided in accordance with higher-ranking layers in particular the packet communication unit and the isochronous communication unit, which should be assigned to the transport layer in the ISO model, are therefore used to fill the defined portions of the data structure of a fixed prespecified length or size, which takes place inside the separating-and-merging unit. Herein, the separating-and-merging unit can, for example, be called a "transmit and receive data interface", therefore with the preferred use of master-slave architecture, it can, for example, be called a "transmit and receive data interface slave" (TARDIS) or a "transmit and receive data interface master" (TARDIM).

In addition to the method and the communication facility, at least one embodiment of the present invention also relates to a medical imaging facility with a plurality of computing facilities and at least one communication facility of the inventive type. All explanations relating to the method and the communication facility can be transferred analogously to the medical imaging facility according to the invention so that the aforementioned advantages can also be achieved thereby.

BRIEF DESCRIPTION OF THE DRAWINGS

Further advantages and details of the present invention can be derived from the example embodiments described below with reference to the drawing, which shows.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

In a method according to an embodiment of the invention for communication between at least two computing facilities of a medical imaging facility, in particular a magnetic resonance facility, via a single communication line it is provided that communication information assigned to different communication types received in each case via a dedicated data input is merged to form data structures of a defined size to be transmitted via the communication line, wherein the data structures are transmitted cyclically with an interval of one cycle time via the communication line and communication information of the different communication types is extracted from data structures received via the communication line and output at data outputs assigned to the respective communication types, wherein the communication types comprise a first packet-oriented communication type and a second isochronous communication type corresponding to isochronous direct channel communication.

A communication facility, according to an embodiment of the invention, for communication between at least two computing facilities of a medical imaging facility, in particular a magnetic resonance facility comprises:
  a communication line and
  for each computing facility in each case a communication-interface assembly connected to the communication line,
wherein the communication interface assemblies in each case a separating-and-merging unit for merging communication information assigned to different communication types received in each case via a dedicated data input into data structures of a defined size to be transmitted via the communication line and for cyclic transmission of the data structures with an interval of one cycle time via the communication line and for the extraction of communication information of the different communication types from data structures of the respective other communication-interface assembly received via the communication line and forwarding to data outputs assigned to the respective communication types, wherein a packet communication unit for the provision and reception of communication information of the first communication type is connected to a data-input-data-output pair assigned to a first packet-oriented communication type and an isochronous communication unit providing and receiving isochronous data as communication information is connected to a data-input-data-output pair assigned to the second communication type corresponding to isochronous direct channel communication. Therefore, the communication facility is embodied to carry out the method according to the invention.

Herein it is noted that, in the context of embodiments of the present invention, a computing facility can obviously also serve as a control facility.

According to an embodiment of the invention, a novel type of communication interface that implements a communication protocol that can be called a UCI (unified communication interface). A UCI is serial point-to-point communication protocol implementing at least two different communication types by way of time-division multiplexing, preferably with the additional use of protection mechanisms. This means that each communication type is assigned a fixed portion (at least one slot) of the data structure (frame) with a fixed invariable size/length. The communication information of the different communication types, which is provided in accordance with higher-ranking layers in particular the packet communication unit and the isochronous communication unit, which should be assigned to the transport layer in the ISO model, are therefore used to fill the defined portions of the data structure of a fixed prespecified length or size, which takes place inside the separating-and-merging unit. Herein, the separating-and-merging unit can, for example, be called a "transmit and receive data interface", therefore with the preferred use of master-slave architecture, it can, for example, be called a "transmit and receive data interface slave" (TARDIS) or a "transmit and receive data interface master" (TARDIM).

It can, therefore, be provided that one separating-and-merging unit is embodied as a master and the at least one further separating-and-merging unit as a slave. Therefore, it is possible to use master-slave architecture with which one of the communication partners acts as a master and the other as a slave; this will be dealt with in more detail below.

Herein, corresponding separating-and-merging units can be already configured in their hardware for the function of master or slave. Herein, the master can have the following tasks: initialization and response of the establishment of the communication link, initialization of packet-oriented communication, transmission and reception of isochronous communication information. The slave can be given the tasks of initialization and response to the establishment of the communication link, response to packet-oriented communication and transmission and reception of isochronous communication data. Herein, it is noted at this point that it is quite feasible to establish isochronous communication between two separating-and-merging units embodied as slaves. In the latter case, the slaves initialize the establishment of the communication link jointly.

Therefore, overall, the communication interface described here enables the grouping and standardization of the communication paths inside a medical imaging facility that provides both high-speed packet-oriented communication and isochronous communication in order to replace the required communication information between the participating components or the computing facilities thereof. Packet-oriented and channel-oriented isochronous transmission is combined on a transmission route, namely the communication line, in order to reduce communication interfaces to a minimum (namely one). This reduces the effort, complexity and costs entailed by communication in the medical imaging facility. In particular, it reduces not only the manufacturing costs but also the maintenance costs for the medical imaging facilities since the cabling is greatly simplified. The fact that it is possible to use the same communication interface or the same communication protocol between different pairs of computing facilities also reduces development effort since the same interface design can be used in all components or for all pairs of computing facilities.

Herein, it is also noted at this point that the separation/merging of the communication information takes place in accordance with the OSI layer model in the data link layer to which, therefore, the separating-and-merging unit is to be assigned. Therefore, the communication protocol described here is transparent to the software used so that there is no need to adapt software components of the computing facilities that are already provided and developed.

In an example embodiment of the present invention, it is provided that streaming communication and/or random access communication for requesting at least one storage register of at least one of the computing facilities are used as a first communication type. Preferably, therefore, three protocols or communication types are unified, namely streaming communication, random access communication and isochronous communication. Therefore, in this embodiment, the communication interface provides:
  a random-access interface for low-access latency,
  a streaming interface for high data throughput and
  an isochronous interface for constant data-transmission latency.

Herein, random access takes place via addressable registers and storage regions. Herein, in master-slave architecture, communication is initiated by a master and answered by an addressed slave. Herein, it can be provided in a first simple embodiment that one access must be completed before a second can start. However, it can also be provided that parallel handling of a plurality of requests takes place in random access communication. This means that support for so-called "split transactions" is also conceivable. As a rule, the service provided by random access communication is used for access to individual registers.

Streaming communication provides a direct data flow between dedicated data sources and data sinks as a further service (streaming access communication). This data channel is preferably used in respect of packet-oriented communication, which is provided by higher protocol layers, in particular the transport layer in the OSI model. This service is preferably subject to flow control in order to avoid FIFO overruns and underruns. As a rule, streaming communication is used for the transmission of mass data as communication information. Streaming communication is preferably symmetrical and full-duplex bidirectional. This means, that a computing facility at a communication-interface assembly can be a data source and a data sink simultaneously.

Finally, isochronous data transmission is offered, wherein this communication service substantially corresponds to a bundle of wires, which transmit signals in parallel and at the same time (isochronously). For example, a constant data rate is ensured since the data flow takes place in real time. The data source and the data sink must be able at all times to provide communication information in a timely manner and receive it in a timely manner. One typical application is magnetic resonance real-time data, in particular the transmission of ADC data or DAC data as communication information, which can also be preprocessed or post processed in individual cases.

In an example embodiment of the invention, it can be provided that at least one prespecified subportion of the data structure, in particular a portion assigned to random access communication, is used to transfer an interrupt, in particular from a slave to a master. While a master can forward any information to a slave, this is more difficult to implement in the opposite direction. If the slave needs to communicate with the master, for example in the case of a condition rendering further communication temporarily impossible, it can be provided that the slave uses the predetermined subportion of the data structure in order to transfer an interrupt, wherein, in response, the master can, for example, pause communication and send a corresponding inquire message relating to the circumstance that has occurred to the slave. Herein, preferably a subportion, for example slot, of the data structure (frame) assigned to random access communication can be preassigned since here a communication type relating to a slower lower data is provided.

As already mentioned, packet-oriented communication between the computing facilities is provided by a packet communication unit, in particular assigned to a transport layer, connected to the data input and the data output of the corresponding communication type. Herein, it can be specifically provided that packet-oriented communication takes place at least partially in accordance with the TCP/IP protocol and/or a proprietary protocol and/or the CAN protocol and/or the CANopen protocol. Obviously, other protocols with communication information provided via the at least one packet communication unit are also conceivable in principle.

In particular in the case of a magnetic resonance facility as a medical imaging facility, it is advantageous for an optical communication line to be used as the communication line within the magnetic resonance room (shielded enclosure), wherein the data structures are converted on both sides by optocouplers. Optical signal transmission not only has the advantage of the high transmission rate, but is also interference-free with respect to other electromagnetic fields, in particular the magnetic fields used in the context of magnetic resonance imaging. The separating-and-merging unit should be connected to an upstream optocoupler, i.e. an optical-electrical converter, in order to receive the electronic signals to be processed or convert them correspondingly into optical signals to be transmitted.

One development of an example embodiment of the invention provides that a dedicated clock-pulse generator is used for each communication type, wherein the clock pulse thereof is in particular derived from a master clock (master clock-pulse generator) of a respective communication-interface assembly. This means that the different communication types can be operated with dedicated clock pulses, in particular selected as application-specific, to which end, for example, a corresponding clock-pulse generator can be provided within the separating-and-merging unit or also within corresponding packet-communication units/isochronous communication units. This clock-pulse generator preferably derives its clock pulse from a basic clock pulse of a master clock (master clock-pulse generator), which is in particular expedient in the context of magnetic resonance, since then a fundamental frequency can be selected as the basic clock pulse of the master clock, wherein this and the multiplies thereof interfere as little as possible with the magnetic resonance imaging. Here, it has been found to be advantageous to select a basic clock pulse or system clock pulse of 2.5 MHz for the master clock; this will be discussed again in more detail with respect to the embodiment of the medical imaging facility as magnetic resonance facility.

As already mentioned, the separating-and-merging unit is embodied for the cyclic transmission of a current data structure in each case after a cycle time. Herein, depending upon the desired data transmission rate, different cycle times can occur, for example a cycle time of 200 ns with 5 GBit/s and a cycle time of 400 ns with 2.5 GBit/s. In the context of at least one embodiment of the present invention, it is, therefore, ensured that a data structure is always transmitted with an interval of one cycle time and a data structure is always received with an interval of one cycle time. Since the data structure is divided into different portions, wherein at least some of the portions are filled with communication information of the different communication types and moreover these portions are fixed, this is also manifested in corresponding time intervals/time windows in which the portions are transmitted by the transmitter or received by the receiver. It is, therefore, possible for different portions of the data structure to be assigned different time windows of the cycle time with respect to transmission. This is in particular useful with respect to isochronous communication.

Expediently, the data structure is provided at its start with a header, as is known in principle from the prior art. Herein, the header portion in the data structure can be selected as relatively small, for example with a magnitude of 4 bytes. Herein, the header, which can also be called the preamble, is followed by the useful data, i.e. the payload, which, at least in the data link layer, is defined as again subdivided, wherein at least some of these portions (slots) are permanently assigned to the respective communication types. The header can also, in restricted form, be used to transfer information.

In an example embodiment of the present invention it is provided that forward error correction (FEC) takes place, wherein forward-error-correction information, in particular based on communication information of all communication types, is created and inserted in a forward-error-correction portion of the data structure, wherein the forward-error-correction information is evaluated on the reception of each data structure. This ensures high transmission security for the communication interface described here or the communication protocol described here. Forward error correction is a technique which is used to reduce the error rate during the transmission of communication information, wherein the transmitter redundantly codes the data to be transmitted by the addition of the forward-error-correction information so that the receiver is able to recognize and correct transmission errors without questioning the transmitter. The redundant coding or the evaluation, which can result in a correction and/or, if correction is not possible, the abortion of communications, are preferably performed by a forward-error-correction facility of the corresponding separating-and-merging units.

Overall, therefore, the data structure in the data link layer can be understood as portions assigned to the communication information of the different communication types, which are bordered by a header and a forward-error-correction portion. Herein, reference is made to the fact that, in the present case, the forward error correction in any case represents an expedient choice since correction of transmission errors "on the fly" is possible without requiring re-transmission. This is because re-transmission of this type would also not be permissible due to the isochronicity of at least the corresponding portion of the communication information. Forward error correction also has a considerable advantage over other protocols with which no error correction of corrupted data or re-transmission of corrupted data is provided.

Preferably, the establishment of a communication link between the computing facilities can also take place by way of a negotiation process at the start of a communication session. Such negotiation processes are in principle already known. In particular, the data structure header mentioned can confirm this successful negotiation. The automated performance of such a negotiation process can also support "hot plugging". This means that, when the computing facilities and hence the communication interface assemblies have been switched on and also when the communication line, for example as an optical fiber, has been plugged in, self-initialization takes place in a secure mode. In the example of the preferred master-slave embodiment, the master can establish the communication link in different steps, wherein, for example, the negotiation of the establishment of the communication link can include a training process with the exchange of basic communication data. However, it is also conceivable for the negotiation process to be operated symmetrically between the master and slave in that each of the two participants notifies its communication interface partner of its dedicated status and the prompts the opposite terminal for the next step.

In one specific embodiment, it is, for example, possible for both separating-and-merging units, in particular therefore the master and the slave, to transmit a basic signal regularly, in particular a byte-alignment signal. On each reception, it is known that both separating-and-merging units are operational and not operating a communication link at present. A byte alignment can then be followed by a word alignment, wherein in the case of a so-called wordlock, the communication link can be considered to be established and basic structures, i.e. frames, can be transmitted. Obviously, it is also possible to use other negotiation processes in the context of at least one embodiment of the present invention.

It is noted that such a negotiation process, which can also be called an initialization sequence, can also be used to interrupt and re-establish a communication link in particular without switching off the communication partners, for example for servicing purposes.

The communication interface described here can not only be used for the connection of two components of the medical imaging facility, but also inside a component, between subcomponents or even inside structural units, for example on a printed circuit board for communication between two chips, for example FPGAs and/or microchips.

In the context of at least one embodiment of the present invention, however, so-called "daisy chaining" is also possible. Herein, a sequence of components or computing facilities are connected in series, wherein communication between all these computing facilities should still be possible. In this case, an expedient development of the invention provides that, in the case of communication between two computing facilities via an intermediate computing facility, these received data structures and/or this communication information are assigned to communication targets and can be forwarded to the communication targets if the communication target does not correspond to the dedicated computing facility. Specifically, it can be provided that at least the communication-interface assembly of the intermediate computing facility comprises an arbitration facility for the assignment of data structures and/or communication information to communication targets and for forwarding to the communication targets if a communication target to not correspond to the dedicated computing facility. Herein, it is obviously also possible for communication information and/or a data structure to have a plurality of communication targets and therefore to be usable both in the intermediate computing facility and in a computing facility connected in series. For example, it is, for example, conceivable for isochronous data streams to be forwarded to two or more computing facilities. The communication targets can in particular be part of the communication information so that, for example, in the case of the separation of communication information in a data structure, the communication targets are identified and if a communication target does not correspond to the dedicated computing facility, the communication information is inserted in a data structure to be forwarded by the or a further separating-and-merging unit.

The communication facility is preferably embodied for communication with a communication rate of at least 1 Gbit/s. For example, it is possible for variants of communication interface assemblies to be created which are configured for a communication rate of 2.5 Gbit/s or a communication rate of 5 Gbit/s. The resulting corresponding time cycles can, for example, be 400 ns or 200 ns. In the context of at least one embodiment of the present invention, it is also conceivable for the communication interface assemblies to be operated with different prespecified communication rates and to be embodied to negotiate a communication rate at the start of a communication session. It can also be possible to provide different transmission rates over the same communication line, which is then configured if required, which is in particular expedient if the communication interface assemblies are to be manufactured and used universally for different communication routes and therefore are not provided in a targeted manner for specific tasks/applications/computing facilities.

The communication interface assemblies, specifically the separating-and-merging units, can be implemented as integrated circuits (ASIC) and/or FPGAs and/or as part of an FPGA. Herein, a particularly advantageous development of at least one embodiment of the present invention provides that the communication interface assemblies are implemented by a computing-facility-specific FPGA, which provides at least a part of the computing power of the computing facility. Such a combination of the communication interface functionality with further functionalities of the computing facility can enable further modules, for example further FPGAs, to be saved, thus greatly reducing manufacturing costs. The corresponding FPGAs are then manufactured specifically for the computing facility, in particular also in respect of specific communication routes and communication information to be received. For example, it is conceivable in respect of a receive unit of a magnetic resonance facility to send communication information received via isochronous communication for further processing in the same FPGA, for example to subject it to at least one evaluation step. In addition to reduced manufacturing costs, such large-scale integration also achieves shorter signal paths and hence faster processing times. Also conceivable are embodiments in which the entire computing facility is provided integrated with the communication-interface assembly.

In addition to the method and the communication facility, at least one embodiment of the present invention also relates to a medical imaging facility with a plurality of computing facilities and at least one communication facility of the inventive type. All explanations relating to the method and the communication facility can be transferred analogously to the medical imaging facility according to the invention so that the aforementioned advantages can also be achieved thereby.

In particular, it can be provided herein that all computing facilities requiring packet-oriented and/or isochronous communication comprise a communication facility of the inventive type for interconnection thereof. This enables communication inside the medical imaging facility to be harmonized and in particular also standardized since the communication interface suggested according to the invention supports both packet-oriented communication and channel-oriented isochronous communication and provides corresponding services. Therefore, using the communication facility according to the invention with the greatest possible degree of consistency reduces the complexity of the medical imaging facility not only because now all that is required is hardware for the corresponding communication links but also in respect of the use of uniform communication interfaces.

At least one embodiment of the present invention can be used particularly advantageously when the medical imaging facility is a magnetic resonance facility.

As already indicated, it can be particularly advantageously provided for a magnetic resonance facility according to the invention of this kind that clock-pulse generators to be used by the communication interface assemblies use a basic clock pulse of a master clock (master clock-pulse generator) that substantially does not interfere with magnetic resonance imaging, in particular a basic clock pulse of 2.5 MHz. Magnetic resonance facilities are extremely sensitive to electromagnetic interference from digital logic. In order to prevent interference with the analog signals to the greatest degree possible, it is suggested that all clock-pulse generators (clocks) be embodied such that the clock pulse or frequency thereof are derived from one single master clock, i.e. from a master clock-pulse generator. Therefore, no local clock-pulse generators or free oscillators are permitted in this embodiment. Herein, the different clock pulses or frequencies are expediently restricted to 2.5 MHz (basic clock pulse or system clock pulse) and integer multiples of 2.5 MHz. Control and data signals preferably do not comprise any repeat patterns in the case of frequencies other than 2.5 MHz or integer multiples of 2.5 MHz. It can in particular be provided in one development that a scrambler facility is provided by the separating-and-merging units in order to clear interference from data signals with potential repetitive patterns that result in unpermitted frequencies.

One specific embodiment of the medical imaging facility embodied as magnetic resonance facility provides that this comprises a central control facility as a first computing facility, which is in particular arranged in a mechanical equipment room and/or a control room outside a shielded magnetic resonance room, computing facilities of at least one gradient unit, at least one transmit unit, at least one receive unit and at least one peripheral unit as second computing facilities and computing facilities of at least one peripheral subunit as third computing facilities, wherein the first computing facility is, in particular as a master, connected in each case via one of the at least one communication facility to the second computing facilities, in particular as a slave, and wherein the peripheral unit, in particular as a master, is connected via in each case one of the at least one communication facility to the third computing facilities, in particular as a slave. This is based on known architecture for magnetic resonance facilities, wherein the communication interfaces used to date, for example PCI Express, USB, RS 232, SPI, proprietary protocols, etc., are replaced in each case by the communication interface described here or the corresponding communication protocol (UCI). In particular, it can be provided in a specific development that the second computing facilities are at least partially connected to one another by at least one of the at least one communication facility. Therefore, it is also possible for "horizontal" data traffic to be provided in particular in a ring, by way of the communication interface suggested here.

As already mentioned, in the magnetic resonance facility, at least inside the magnetic resonance room, the communication preferably takes place via optical communication lines. For example, it is possible to use fiber-optic full-duplex cables with a single glass fiber for each communication direction for the communication lines thus, for example, enabling physical transmission rates of 2.5 GBit/s, 5 GBit/s or even 10 GBit/s to be provided.

Reference is also made to the fact that the communication structure suggested here at least partially uses the above-discussed daisy chaining method for the magnetic resonance facility so that, therefore, as described, it is preferably possible to use corresponding arbitration facilities at least partially.

Figure 1:
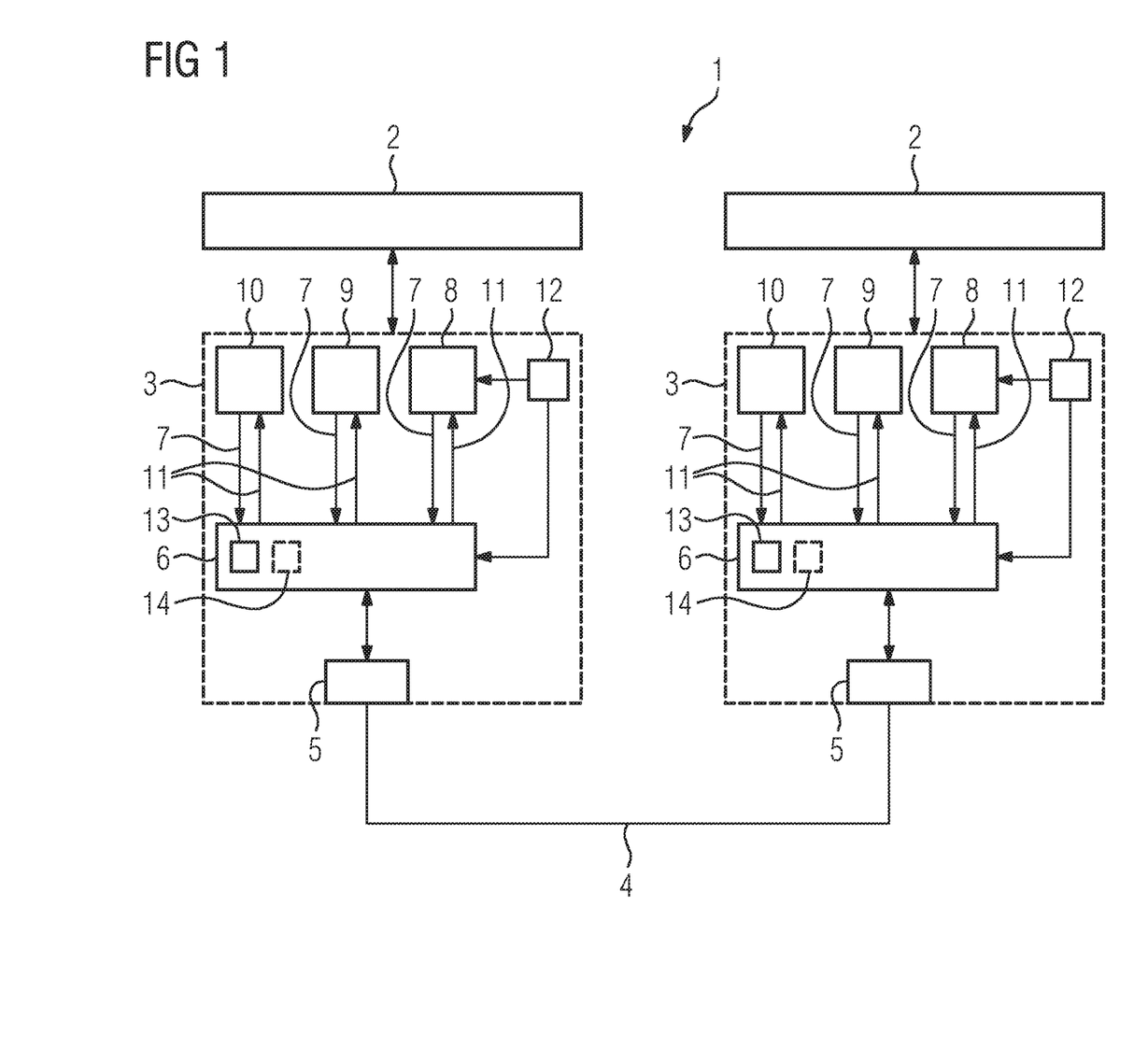
FIG. 1 a schematic sketch of a communication facility according to an embodiment of the invention, FIG. 2 the subdivision of a data structure used and FIG. 3 the communication structure of a magnetic resonance facility.

FIG. 1 is a schematic sketch of an example embodiment of a communication facility according to the invention 1, which is used for communication between two computing facilities 2 belonging to components of a magnetic resonance facility as a medical imaging facility. The communication facility 1 comprises for each of the computing facilities 2 a communication-interface assembly 3, wherein the communication interface assemblies 3 are connected by a communication line 4, which, for electrical data transmission, can be embodied as a conventional electric cable, inside a magnetic resonance room, but is preferably embodied as an optical communication line 4 that is full-duplex compliant and therefore comprises a glass fiber for each communication direction.

In the case of the optical communication line 4 depicted here, the communication-interface assembly 3 first comprises an optocoupler 5 (optoelectronic transducer). The core of the communication-interface assembly 3 is a separating-and-merging unit 6, which is correspondingly connected in each case to the optocoupler 5.

The separating-and-merging unit 6 is first used to merge communication information of different communication types of which at least one is packet-oriented communication and at least one is isochronous communication to form common data structures with a fixed subdivision and fixed size, which are to be transmitted via the single communication line 4, wherein the data structures are always transmitted with an interval of exactly one cycle time, for example 200 ns or 400 ns. The communication information is provided to the separating-and-merging unit 6 via data inputs 7 of corresponding units of the transport layer, while the separating-and-merging unit 6 is to be assigned to the data link layer.

Since in the present case, the communication types to be provided are isochronous communication corresponding to an isochronous direct channel link via the common communication interface described here, streaming communication and random access communication, the communication-interface assembly 3 comprises an isochronous communication unit 8, which provides isochronous communication information via the corresponding data input 7, and two packet-communication units 9, 10 in each case for streaming communication and random access communication. These units are ultimately those that will be addressed by the computing facilities 2; the separating-and-merging unit 6 is ultimately "invisible" to the application in the computing facilities 2". The packet-communication units 9, 10 can be used to implement different specific packet-oriented communication protocols, for example TCP/IP, CAN/CANopen, proprietary protocols and the like.

Therefore, in the case of reception, the separating-and-merging unit 6 is also used to re-separate the corresponding communication information from the received data structures and provide it via corresponding data outputs 11 of the isochronous communication unit 8 and the packet-communication units 9, 10. A data input 7 and data output 11 pair forms an internal interface for the corresponding communication information assigned to the communication site.

Since the example embodiment of the communication facility 1 depicted in FIG. 1 is to be used in a magnetic resonance room of a magnetic resonance facility, care should be taken to ensure the greatest possible freedom from interference in respect to the electric signals used in the communication interface assemblies 3. Therefore, a master clock 12 operated with a fundamental frequency of 2.5 MHz is provided as the sole clock-pulse generator. Inside the communication-interface assembly 3, only integer multiples of this fundamental frequency of 2.5 MHz are permitted, wherein the communication units 8-10 assigned to the different communication types can quite possibly comprise a dedicated clock-pulse generator, which is not shown in further detail here, if a dedicated clock pulse or dedicated frequency is to be used in each case. However, herein, these clock-pulse generators use the signal of the master clock 12.

The separating-and-merging unit 6 can also analyze whether recurrent patterns in the communication information or the data structures formed can cause other frequencies to form, wherein they can comprise a scrambler facility, which, in the case of doubt, can ensure such interfering frequencies are eliminated or carries out suitable equalization on the receive side.

The separating-and-merging unit 6 further comprises a forward-error-correction facility 13, which processes all communication information with respect to forward error correction. In the case of daisy chaining with which a plurality of computing facilities 2, which are connected by respective communication facilities 1, are serially connected, it is also possible for an arbitration facility 14 to be provided as will be discussed in more detail below.

The communication interface assemblies 3 can, for example, be implemented as plug-in cards or at least on a common printed circuit board. Particularly preferably, at least some portions of the communication interface assemblies 3 are implemented as an FPGA or part of an FPGA—this applies in particular to the separating-and-merging unit 6 and the isochronous communication unit 8 and the packet-communication units 9, 10. In particular, an embodiment is conceivable in which the units 6, 8-10 are implemented inside a single FPGA, which also implements at least some of the functions of the computing facility 2, i.e. provides a part of the computing power thereof. This is of particular interest in respect of isochronous communication information since isochronous communication information can be further processed directly and without excessive time delay.

The communication facility 1 is embodied to carry out the method according to an embodiment of the invention. Therefore, to be specific, communication information of the corresponding communication types received by the packet information units 9, 10 and the isochronous communication unit 8 are combined in data structures together with forward-error-correction information and a header, wherein the data structures are transmitted cyclically via the communication line 4, wherein a corresponding separation of the data structures including forward error correction is performed inside the receiving separating-and-merging unit 6. In the present case, a master-slave architecture is used which one of the separating-and-merging units 6 functions as a master and the other as a slave. Herein, packet-oriented communication types are initiated by the master.

Figure 2:
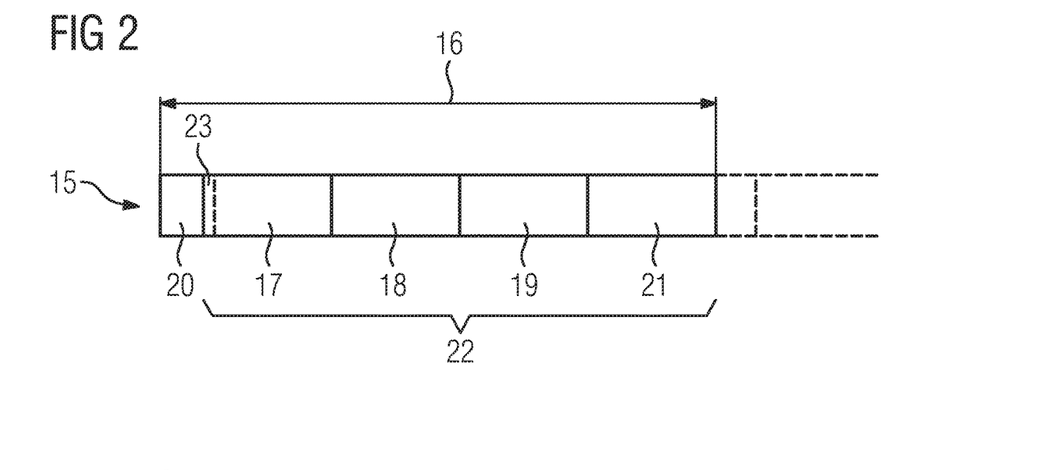

FIG. 2 is a schematic depiction of a possible subdivision of the data structure 15 of a prespecified size. Dashed lines also indicate a subsequent data structure, which is emitted after the expiry of the cycle time 16.

The data structure 15 comprises defined portions 17, 18 and 19 for communication information, wherein the portion 17 is provided for communication information of the random access communication, the portion 18 for communication information of streaming communication and the portion 19 for communication information of isochronous communication. The portions 17-19 are bordered by a header 20 and a forward-error-correction portion 21 for the forward-error-correction information, as described. The portions 17, 18, 19 and the forward-error-correction portion 21 form the useful data (payload) 22 at the physical level.

In one specific embodiment, the data structure 15 (frame) can be made up of 25 slots (No 0 to No 24) of four bytes each. The first slot (No 0) can be assigned to the header, the next three slots to the portion 17, the next three slots to the portion 18 the next sixteen slots to the portion 19. The two final slots can be reserved for the forward-error-correction information in the forward-error-correction portion 21. Obviously other frame lengths and/or other divisions of the overall bandwidth are also conceivable.

Herein, the communication facility 1 can implement physical data transmission rates of 2.5 GHz/s, 5 GHz/s or 10 GHz/s (even higher data rates), wherein the corresponding cycle times are 400 ns, 200 ns or 100 ns. Also conceivable is an embodiment in which the communication facility 1 can be configured to provide a plurality of data transmission rates, wherein a corresponding data transmission rate can be defined as required when negotiating the communication link.

With serial transmission of the data structures 15, it is ensured that a header 20 always arrives with an interval of one cycle time 16 and, therefore, this is also applicable for corresponding time windows of the cycle time for the corresponding other portions 17, 18, 19 and the forward-error-correction portion 21.

In summary, therefore, it can be stated that a communication protocol is provided at the physical level, which can be called a point-to-point serial communication protocol, which securely transmits communication information of three different communication types by time-division multiplexing due to forward error correction.

FIG. 2 also shows a special feature of the embodiment shown here. A subportion 23, for example slot, of the portion 17 of the random access communication is reserved for the implementation of an interrupt function by which the slave can send the master an interrupt.

It is mentioned at this point, that for random access via addressable registers or storage regions, which are not depicted in further detail here, it can be provided that one access must be first completed before a second access can commence. However, also conceivable are embodiments in which "split transactions" are possible. Furthermore, the communication link described here and created by a negotiation process is full-duplex bidirectional so that both sides are able to transmit and receive simultaneously.

Figure 3:
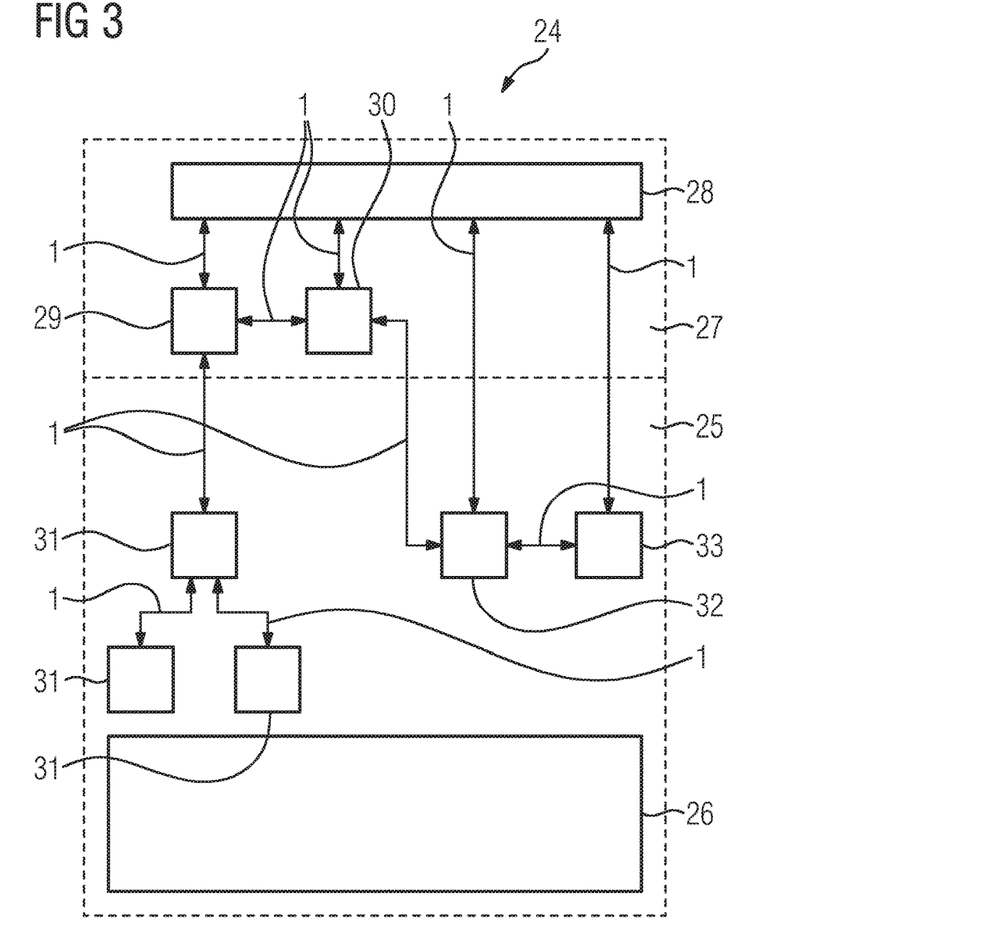

FIG. 3 is a schematic depiction of the communication structure of magnetic resonance facility 24 as a medical imaging facility according to an embodiment of the invention. As is known in principle, a main magnetic unit 26 including the actual imaging components is arranged in a magnetic resonance room 25. There is also a mechanical equipment room 27 in which a control facility 28 is provided as a control computer. This central control facility 28 controls the operation of the magnetic resonance facility 24 and herein communicates directly or indirectly with further components of the magnetic resonance facility 24 or the computing facilities 2 thereof. Herein, a peripheral unit 29 and a gradient unit 30 are shown as further components in the mechanical equipment room 27.

In addition to peripheral subunits 31, a transmit unit 32 and a receive unit 33 are located in the magnetic resonance room 25. Provided between the central control computer 28 as a first computing facility, or as comprising the first computing facility, and the computing facilities of the components peripheral unit 29, gradient unit 30, transmit unit 32 and receive unit 33 as second computing facilities is in each case a communication facility 1 and in similarly between the computing facility of the peripheral unit 29 and the computing facilities of the peripheral subunits 31 as third computing facilities. Further communication facilities 1 are provided between the second computing facilities, wherein here it is also possible for an enclosed communication ring to be provided.

It is evident with the communication structure shown in FIG. 3 that daisy chaining is used at least partially so that, at least in the peripheral unit 29, but also when, for example, the receive unit 33 includes a digital receive unit and an analog receive unit, the intermediate facility in each case comprises a communication-interface assembly 3 with an arbitration facility 14. This establishes the communication targets of communication information and forwards the communication information if the communication target does not correspond to the dedicated computing facility.

It is also noted that, in addition to magnetic resonance data per se, isochronous communication can also be expedient with peripheral units 29, 31, for example for the reception of physiological scan data for the patient or the like.

The communication facility described here, and therefore the communication interface, permits standardized, simultaneous packet-oriented and channel-oriented communication on a single communication line 4. In particular, the same communication interface or communication facility 1 can be used in the entire resonance facility 24 thus reducing complexity, development costs and the like.

Although the invention was described in more detail by the preferred example embodiment, the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for communication between at least two computing facilities of a medical imaging facility, via a single communication line, the method comprising:
   merging communication information, assigned to respective different communication types received via a dedicated data input, to form data structures of a defined size to be transmitted via the single communication line;
   transmitting the data structures, cyclically with an interval of one cycle time, via the single communication line;
   extracting communication information of the respective different communication types from data structures received via the communication line; and
   outputting the communication information extracted at data outputs assigned to the respective different communication types, wherein the respective different communication types include a first packet-oriented communication type and a second isochronous communication type corresponding to isochronous direct channel communication,
   wherein at least one prespecified subportion of the data structure is used to transfer an interrupt, wherein at least one prespecified subportion of the data structure is used to transfer an interrupt from a slave to a master.

2. The method of claim 1, wherein at least one of streaming communication and random access communication for requesting at least one storage register of at least one of the at least two computing facilities are used as a first communication type of the respective different communication types.

3. The method of claim 2, wherein parallel handling of a plurality of requests takes place in the random access communication.

4. The method of claim 1, wherein an optical communication line is used as the communication line and wherein the data structures are converted on both sides by optocouplers.

5. The method of claim 1, wherein forward error correction takes place, wherein forward-error-correction information is generated and inserted in a forward-error-correction portion of the data structure, and wherein the forward-error-correction information is evaluated upon reception of each of the data structures.

6. The method of claim 1, wherein, for communication between two computing facilities via an intermediate computing facility, at least one of data structures and communication information received by at least one of data structures, are assigned to communication targets and forwarded to the communication targets upon a communication target not corresponding to a dedicated computing facility of the two computing facilities.

7. A magnetic resonance facility, comprising:
a plurality of computing facilities, a central control facility as a first computing facility of the plurality of computing facilities, being arranged in at least one of a mechanical equipment room and a control room outside a shielded magnetic resonance room; and
at least one communication facility for communication between at least two computing facilities of a medical imaging facility, including:
a communication line, and
a plurality of communication interface assemblies including a communication-interface assembly, connected to the communication line, for each respective computing facility of the at least two computing facilities, the plurality of communication interface assemblies being implemented as at least one of Application-Specific Integrated Circuit (ASIC), Field Programmable Gate Arrays (FPGA) and as part of an FPGA, and each of the respective plurality communication interface assemblies including
a separating-and-merging unit for merging communication information assigned to respective different communication types received via a dedicated data input into data structures of a defined size to be transmitted via a communication line and for cyclic transmission of the data structures with an interval of one cycle time via the communication line and for extraction of communication information of the respective different communication types from data structures of a respective other communication-interface assembly received via the communication line and forwarding to data outputs assigned to the respective different communication types,
a packet communication unit for provision and reception of communication information of a first communication type of the respective different communication types, connected to a data-input-data-output pair assigned to a first packet-oriented communication type, and
an isochronous communication unit providing and receiving isochronous data as communication information, connected to a data-input-data-output pair assigned to a second communication type of the respective different communication types, corresponding to isochronous direct channel communication;
computing facilities of at least one gradient unit, at least one transmit unit, at least one receive unit and at least one peripheral unit as second computing facilities of the plurality of computing facilities; and
computing facilities of at least one peripheral subunit as third computing facilities of the plurality of computing facilities, wherein the first computing facility is a master, respectively connected, via one of the at least one communication facility, to the second computing facilities as a slave, and wherein the peripheral unit is respectively connected, via in each case one of the at least one communication facility, to the third computing facilities as a slave.

8. The magnetic resonance-facility of claim 7, wherein the plurality of computing facilities, wherein all computing facilities of the plurality of computing facilities, requiring at least one of packet-oriented communication and isochronous communication, include the at least one communication facility.

9. A magnetic resonance facility, comprising:
a plurality of computing facilities; and
at least one communication facility for communication between at least two computing facilities of a medical imaging facility, including:
a communication line, and
a plurality of communication interface assemblies including a communication-interface assembly, connected to the communication line, for each respective computing facility of the at least two computing facilities, the plurality of communication interface assemblies being implemented as at least one of Application-Specific Integrated Circuit (ASIC), Field Programmable Gate Arrays (FPGA) and as part of an FPGA, and each of the respective plurality communication interface assemblies including
a separating-and-merging unit for merging communication information assigned to respective different communication types received via a dedicated data input into data structures of a defined size to be transmitted via a communication line and for cyclic transmission of the data structures with an interval of one cycle time via the communication line and for extraction of communication information of the respective different communication types from data structures of a respective other communication-interface assembly received via the communication line and forwarding to data outputs assigned to the respective different communication types,
a packet communication unit for provision and reception of communication information of a first communication type of the respective different communication types, connected to a data-input-data-output pair assigned to a first packet-oriented communication type, and
an isochronous communication unit providing and receiving isochronous data as communication information, connected to a data-input-data-output pair assigned to a second communication type of the respective different communication types, corresponding to isochronous direct channel communication;

wherein clock-pulse generators, usable by the communication interface assemblies, use a fundamental frequency of a master clock that substantially does not interfere with the magnetic resonance imaging.

10. The magnetic resonance facility of claim 7, wherein ones of the second computing facilities are at least partially connected to other of the second computing facilities by at least one of the at least one communication facility.

11. The method of claim 1, wherein the method is for communication between at least two computing facilities of magnetic resonance facility.

12. The method of claim 1, wherein the at least one prespecified subportion of the data structure includes a subportion of a portion assigned to random access communication.

13. The magnetic resonance facility of claim 9, wherein clock-pulse generators use a fundamental frequency of 2.5 MHz.

14. The magnetic resonance facility of claim 9, wherein ones of the plurality of computing facilities are at least partially connected to other of the plurality of computing facilities by at least one of the at least one communication facility.

15. The magnetic resonance facility of claim 7, wherein the plurality of communication interface assemblies are implemented by a computing-facility-specific FPGA providing at least one part of computing power of the computing facility.

* * * * *